United States Patent
Fructus et al.

(10) Patent No.: US 8,784,298 B2
(45) Date of Patent: Jul. 22, 2014

(54) INSTRUMENT FOR AN ENDOSCOPE

(75) Inventors: Olivier Fructus, Nazelles Negron (FR); Nicolas Mathieu, Ecully (FR)

(73) Assignee: Axess Vision Technology, Tours (FR)

( * ) Notice: Subject to any disclaimer, the term of this patent is extended or adjusted under 35 U.S.C. 154(b) by 435 days.

(21) Appl. No.: 13/060,107

(22) PCT Filed: Sep. 1, 2009

(86) PCT No.: PCT/FR2009/051649
§ 371 (c)(1),
(2), (4) Date: Mar. 15, 2011

(87) PCT Pub. No.: WO2010/023416
PCT Pub. Date: Mar. 4, 2010

(65) Prior Publication Data
US 2011/0184233 A1     Jul. 28, 2011

(30) Foreign Application Priority Data
Sep. 1, 2008 (FR) ...................................... 08 55854

(51) Int. Cl.
*A61B 1/00* (2006.01)

(52) U.S. Cl.
USPC .......................................... 600/104; 600/114

(58) Field of Classification Search
USPC ......... 600/104, 114, 127, 128, 130, 153, 154; 604/14
See application file for complete search history.

(56) References Cited

U.S. PATENT DOCUMENTS

| | | | |
|---|---|---|---|
| 5,025,778 A * | 6/1991 | Silverstein et al. | 600/104 |
| 5,257,617 A | 11/1993 | Takahashi | |
| 5,503,616 A | 4/1996 | Jones | |
| 5,876,329 A | 3/1999 | Harhen | |
| 2007/0142709 A1 | 6/2007 | Martone et al. | |
| 2009/0264703 A1 * | 10/2009 | Pribanic | 600/121 |

FOREIGN PATENT DOCUMENTS

JP     2003339624     12/2003

* cited by examiner

*Primary Examiner* — Anhtuan T Nguyen
*Assistant Examiner* — Rynae Boler
(74) *Attorney, Agent, or Firm* — Ladas & Parry LLP

(57) ABSTRACT

An endoscope instrument includes an insertion tube of longitudinal axis possessing a proximal portion for connection to an actuation support and a distal portion presenting an outlet section occupied by a viewing zone and by at least one outlet orifice for passing at least one appliance for occupying a retracted position inside the tube and a working position in which the appliance occupies at least a portion of the outlet section. The distal portion of the insertion tube includes at least one radially deformable wall over a portion of its length extending from the outlet section, enabling the outlet section of the distal portion of the tube to be increased on the appliance passing from its retracted position in which the appliance does not stress the deformable wall to its working position in which the deformable wall is stressed radially.

12 Claims, 2 Drawing Sheets

INSTRUMENT FOR AN ENDOSCOPE

BACKGROUND OF THE INVENTION

The present invention relates to the technical field of instrumentation covering all fields of activity and serving to provide access or illumination, or to examine the inside of a body in the general sense, such as a cavity or a channel.

More precisely, but not exclusively, the present invention relates to an instrument for a medical endoscope for single use or multiple use, serving to illuminate and to examine the inside surface of a hollow organ, cavity, or natural or artificial duct in the human body for therapeutic, surgical, or diagnostic purposes.

The instrument of the invention is used for diagnostic or surgical purposes to inspect any internal portion of the human body that can be accessed via natural or artificial paths. For example, the endoscope instrument of the invention may be used in the field of urinary tract, gastrointestinal tract, the respiratory system, the cardiovascular system, the trachea, the sinus cavity, the reproductive system in women, the abdominal cavity, or any other portion of the human body for investigating via a natural or an artificial path.

In the above technical field, various types of endoscope exist that are adapted to organs that are accessible for observing. In general, an endoscope comprises a more or less flexible insertion tube possessing a proximal portion for connection to an actuation support that enables the tube to be steered inside the insertion path. The endoscope also includes a display system, generally an optical display system, that serves to illuminate and to examine the organ, the cavity, or the duct of the human body from the distal portion of the insertion tube. In numerous applications, it is found to be advantageous to bring one or more appliances to the distal portion of the insertion tube, in association with the access, lighting, and observation zone, the appliance(s) being adapted to enable various functions to be performed such as: delivering fluid; delivering instruments; taking samples; or performing surgical operations. The distal portion of the insertion tube thus presents an outlet section that is occupied in part by the lighting and observation zone, and in part by the orifice for passing one or more appliances.

It should be considered that the outlet section of the distal portion of the insertion tube presents a magnitude that is limited by the smallest width of the natural or artificial access path in which the insertion tube is engaged.

Even though the miniaturization of appliances is continuously making advances, the development of ever more complex appliances requires a relatively large section for passing the appliance in the distal portion of the insertion tube. In analogous manner, the need to obtain an image of good quality requires a lighting and observation zone of sufficient area to be available at the distal portion of the insertion tube.

In an attempt to remedy those opposing constraints, international patent application WO 2005/104927 proposes an endoscope having an insertion tube in which the distal portion is fitted with hinge means that enable tooling and/or the optical observation system to be deployed radially. It should be observed that that technical solution can be implemented only in the context of a hollow organ of section that is greater than the section of the endoscope access path. It should be considered that the operation of hinge means requires a relatively large deployment zone to be available, thereby limiting the use of that endoscope. In addition, radial deployment of the hinge means might damage the tissue of the inspected organ. Furthermore, the hinge means are found to move in random manner and to be difficult to control. Finally, the distal portion of the insertion tube is found to be difficult to decontaminate thoroughly.

For the same purpose, U.S. Pat. No. 5,025,778 describes an endoscope having an insertion tube with deformable tubing engaged on its outside over its entire length, the tubing being arranged in an expanded position to define at least one passage channel. Before the endoscope is inserted in the patient, the channel is not formed such that the deformable tubing is pressed against the insertion tube. After the endoscope has been inserted in the patient, a fluid or a tubular element is moved along the passage channel in order to put it into its expanded position.

In similar manner, U.S. Pat. No. 5,503,616 describes an endoscope having an insertion tube with a deformable membrane fitted to the outside thereof over its entire length, the membrane being arranged, when in an expanded position, to define a channel for passing equipment.

Those technical solutions increase the section of the endoscope for passing an appliance by adding tubing or a deformable membrane to the insertion tube, the tubing or the membrane then not being configured in its expanded position. The extra thickness fitted on the insertion tube makes it necessary, for a given through section in the access path, to reduce the size of the insertion tube and consequently to limit or reduce the size of the appliances and/or the viewing system.

Furthermore, those technical solutions give rise to an increase in the through section of the endoscope over the entire length of the insertion tube, and sometimes that is not possible or at the least runs the risk of discomforting the patient or damaging tissue around the access path.

The present invention thus seeks to remedy the above-specified drawbacks by proposing an endoscope instrument in the general sense, and more particularly for use in the medical field, the instrument presenting a miniaturized distal portion providing good quality observation and the possibility of bringing various appliances to said distal portion while avoiding damage to the surrounding organs or tissue.

Another object of the invention is to provide an endoscope instrument in which the insertion tube does not present extra thickness and that is suitable for optimizing use of the space available in the access path in the patient through which the endoscope passes.

To achieve this object, the endoscope instrument comprises an insertion tube of longitudinal axis possessing a proximal portion for connection to an actuation support and a distal portion presenting an outlet section occupied in particular firstly by a viewing zone and secondly by at least one outlet orifice for passing at least one appliance for occupying a retracted position inside the tube and a working position in which the appliance occupies at least a portion of the outlet section. According to the invention, the distal portion of the insertion tube includes at least one radially deformable wall over a portion of its length extending from the outlet section, thereby enabling the outlet section of the distal portion of the tube to be increased on the appliance passing from its retracted position in which the appliance does not stress the deformable wall to its working position in which the deformable wall is stressed radially, the outlet section of the distal portion corresponding to the right cross-section of the insertion tube in the retracted position of the appliance.

According to an advantageous embodiment characteristic, the distal portion of the insertion tube is provided with a sealing member closing the outlet orifice of the passage for the appliance. This sealing member serves to avoid contaminating the appliance throughout the insertion movement of the insertion tube, or to keep the appliance sterile.

For example, the sealing member is a plug that is ejectable or a membrane that is tearable by the appliance or by fluid pressure.

In another embodiment, the appliance comprises at least one tubular duct mounted inside the insertion tube so as to be slidable relative to the insertion tube.

The appliance includes at least one tool optionally mounted in the tubular duct.

In another variant, the distal portion of the tubular duct is provided with at least one sealing envelope.

For example, the sealing envelope presents mechanical strength that is greater than that of the sealing member carried by the distal portion of the insertion tube.

In another example, the sealing envelope of the tubular duct is an envelope that is tearable by the tooling housing inside the tubular duct.

According to an embodiment characteristic, the insertion tube includes, in its distal portion, a guide system for guiding the appliance in order to enable the deformable wall to be expanded radially during the movement of the appliance.

In an embodiment, the distal portion of the insertion tube is embedded in a deformable material internally defining the passage for the appliance.

In a preferred embodiment, the distal portion of the insertion tube includes a viewing system.

It should be observed that the distal portion or head of the instrument is optionally removable relative to the insertion tube.

For example, the viewing system is embedded in the deformable material.

The invention also proposes an endoscope provided with an instrument in accordance with the invention.

Various other characteristics appear from the following description with reference to the accompanying drawings that show embodiments of the invention as non-limiting examples.

DETAILED DESCRIPTION OF THE INVENTION

Figure 1:
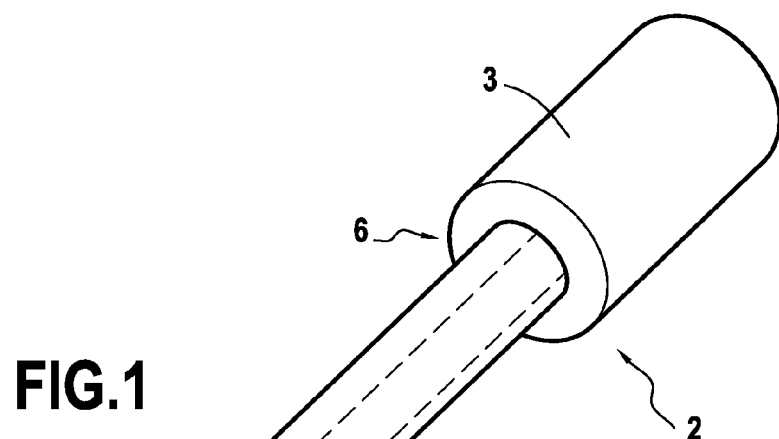
FIG. 1 is a diagrammatic view of a first embodiment of an endoscope instrument in accordance with the invention.

As can be seen more clearly in FIG. 1, the invention relates to an instrument 1 for an endoscope 2 that is adapted to examining the inside of a body in the general sense. Preferably, the instrument 1 of the invention is particularly adapted to be implemented in medical applications, and thus to be fitted to a medical endoscope making it possible to access and inspect any portion of the human body from a natural or artificial access path. Naturally, the endoscope 2 serves to illuminate and inspect the inside surface of a hollow body, a cavity, or a duct in the human body for therapeutic, surgical, or diagnostic purposes. It should be understood that the instrument 1 is adapted to fit various types of endoscope that are adapted to organs that are accessible via a natural path such as a laryngoscope, a bronchoscope, an esophageoscope, a gastroscope, a duodenoscope, a cystoscope, a hystereoscope, and a coloscope, for example. Naturally, the instrument 1 is adapted to give access to other internal portions of the human body via paths that are formed artificially in the human body.

In conventional manner, a medical endoscope 2 comprises an actuator block or support 3 that is generally in the form of a handle or a robot arm, and that is fitted with an instrument 1 in accordance with the invention. The instrument 1 is integrally mounted, or preferably separably mounted on the actuation support 3. In the preferred example of separate mounting, the endoscope 2 includes, between the instrument 1 and the actuation block 3, a connection and disconnection system that is adapted to provide a temporary and at least mechanical connection quickly, while also providing the advantage of enabling the instrument 1 to be separated easily from the support 3. The connection and disconnection system is not described insofar as it is well known to the person skilled in the art and does not specifically form part of the subject matter of the invention.

Figure 2:
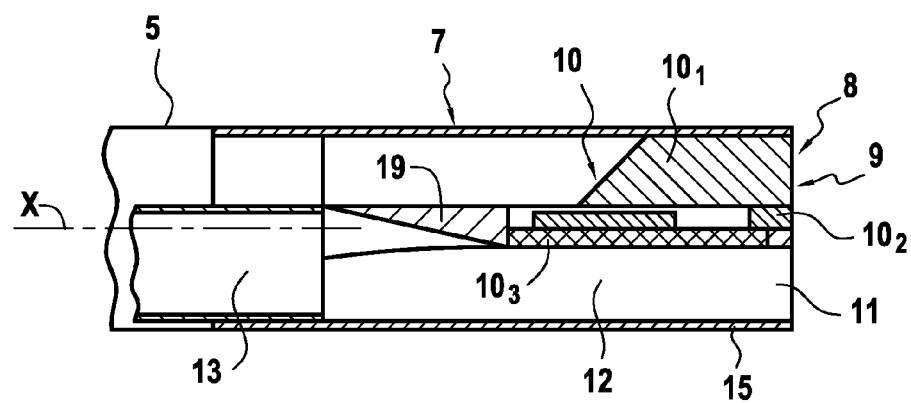
FIG. 2 is a fragmentary elevation view in section of the distal portion of the instrument as shown in FIG. 1.

As can be seen more clearly in FIGS. 1 and 2, the instrument 1 includes an insertion tube 5 that extends along a longitudinal axis X and that is of right cross-section that is preferably circular. The insertion tube 5 is flexible to a greater or lesser extent and it is made of a biocompatible material. The insertion tube 5 possesses a proximal portion 6 for connection to the actuation support 3 and an opposite distal portion 7 forming the head of the instrument 1. Advantageously, the endoscope 2 includes a device enabling the distal portion 7 of the instrument 1 to be folded or deflected. The actuation device (not shown but made of any suitable material) generally comprises one or more actuation cables fastened to the distal portion 7 of the instrument and connected to an actuation system mounted in the support 3.

As can be seen more clearly in FIG. 2, the distal portion 7 of the instrument 1 presents at its free end a transverse face 8 that defines the outlet section of the head 7. This outlet section 8 is occupied in particular firstly by a viewing zone 9 and secondly by at least one orifice 11 of a passage 12 for at least one appliance 13, there being only one such orifice in the example shown. In the example shown in the drawings, the transverse face 8 extends substantially perpendicularly to the longitudinal axis X of the tube 5. Naturally, the transverse face 8 could extend in more or less inclined manner relative to the longitudinal axis X.

The viewing zone 9 comprises a portion of the transverse face 8 of the distal portion 7 from which a viewing system 10 serves to observe or inspect an internal portion of the human body. Advantageously, the viewing system 10 is an imaging system. For example, the viewing system 10 comprises an image-forming system $10_1$ mounted inside the distal portion 7 and connected to a transmission bundle extending inside the tube 5 and communicating with a unit for acquiring and processing images. For example, the image-forming system $10_1$ comprises one or more optical lenses connected to any type of image transmission. Preferably, the observation optical system 10 includes lighting $10_2$ including a light source such as a light-emitting diode (LED) fastened to a printed circuit $10_3$. Naturally, the lighting $10_2$ is connected to an electrical connection bundle extending inside the tube 5 so as to be connected upstream from the proximal portion 6 of the instrument to a source of electricity. In the above-described embodiment, the viewing system 10 is of an optical nature and it preferably provides its own lighting, however it is clear that the viewing system 10 could be made in some other way.

For example, the viewing system 10 could implement an ionizing system or a radiating system, such as one using ultrasound.

Figure 3:
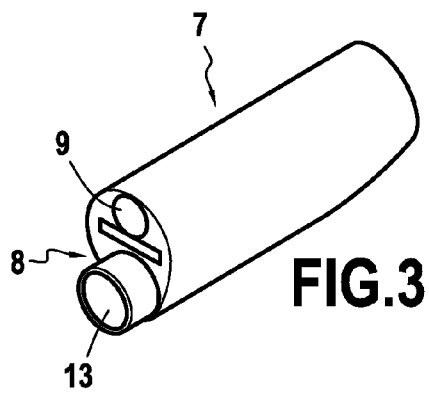
FIGS. 3 and 4 are fragmentary views respectively in perspective and in section and in elevation of the instrument in accordance with the invention in a working position.
Figure 4:
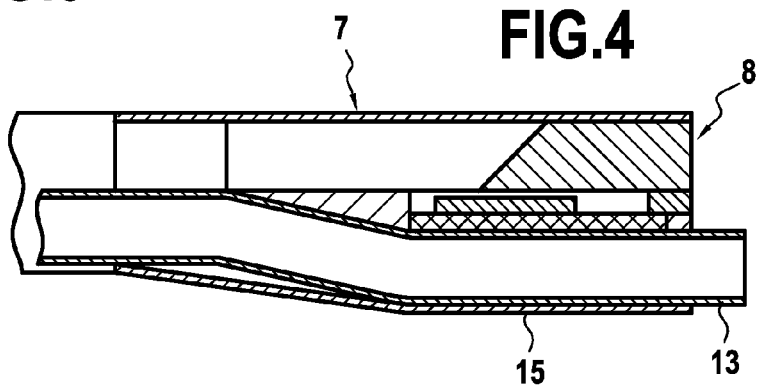

The appliance 13 is designed to occupy a retracted position inside the insertion tube 5, as shown in FIGS. 1 and 2, and a working position as shown in FIGS. 3 and 4, in which the appliance 13 occupies at least a portion of the outlet section 8. In general, the appliance 13 with which the instrument 1 is fitted depends on the nature of the operation(s) to be performed by the endoscope. In non-limiting manner, the appliance 13 corresponds to one or more pieces of equipment or kit, tools, sensors, or accessories. This appliance 13 may be usable in a variety of fields and for example it may be mechanical, electrical, calorific, magnetic, chemical, fluidic, solid, etc. in order to perform a variety of operations such as, for example: incisions; destructions; sample taking; measurements; delivering a material (gas, liquid, solid).

In the embodiment shown, the appliance 13 comprises a tubular duct mounted inside the insertion tube 5 so as to slide relative to the tube 5. The tubular duct is connected to any appropriate means enabling relative sliding of the tubular duct inside the insertion tube 5. The tubular duct thus enables all types of equipment, tooling, or kit of any kind to be taken to the end of the insertion tube 5. This equipment etc. may be fitted to or mounted inside the insertion tube 5. For example, when delivering a fluid to the distal portion of the instrument, the tubular duct may be connected to a fluid feed source at the proximal portion of the instrument and/or may incorporate a quantity of fluid and/or of material for delivery at the distal end of the instrument 1.

Naturally, the appliance 13 may include one or more tubes in which equipment etc. is mounted. Furthermore, the appliance 13 may include equipment etc. that is mounted directly inside the insertion tube 5, i.e. the appliance 13 does not have a tubular duct. When the appliance 13 comprises a plurality of pieces of equipment etc., they may extend from the distal portion 7 through the same orifice 11 or through a plurality of orifices 11 of passages 12 that communicate with the inside of the insertion tube 5.

In accordance with the invention, the distal portion 7 of the insertion tube 5 includes, over a fraction of its length, and starting from its outlet section 8, at least one radially-deformable wall 15 enabling the outlet section 8 of the distal portion of the tube to be increased when passing at least one appliance 13 from its retracted position to its working position. This deformable wall 15 is made in any suitable manner for allowing the distal portion 7 of the tube 5 to extend radially on taking the appliance 13 to the outlet section 8.

Naturally, the right cross-section of the appliance 13 is advantageously greater than the right cross-section of the outlet orifice 11 at rest or in the retracted position of the appliance 13. The retracted position of the appliance 13 is selected to be upstream from the outlet section 8 at a location that does not affect the right cross-section of the insertion tube 5. In the example shown in FIG. 2, the retracted position of the appliance 13 is shown diagrammatically at the inlet of the distal portion 7, however it is clear that the retracted position could correspond to any position inside the instrument 1 or the support 3.

In the embodiment shown, the deformable wall 15 is made from a deformable material constituting the distal portion 7 of the insertion tube. In this embodiment, the distal portion 7 is in the form of a block or sleeve in which the viewing system 10 is embedded. In this example, the block of material defines an internal bore to form the passage 12 that communicates with the inside of the tube 5 and that opens to the outside via the outlet orifice 11.

In this embodiment, the distal portion 7 is thus in the form of a block of a flexible material in which the viewing system 10 is embedded and it serves to define the passage 12 for the appliance. The distal portion 7 is connected by any suitable means to the insertion tube 5. The distal portion or head 7 is connected to the insertion tube 5 via temporary or permanent assembly means. Thus, the distal portion 7 may optionally be removable relative to the insertion tube 5. The distal portion or head 7 is thus mounted to extend the insertion tube 5 by presenting, in the retracted position of the appliance 13, a right cross-section that is equal to the right cross-section of the insertion tube 5.

Naturally, the radially deformable wall 15 may be made in some other way. By way of example, the deformable wall 15 may be made as a flexible diaphragm fastened on a rigid body. Under such circumstances, the distal portion 7 constitutes an essentially rigid body fitted with the deformable wall 15. The deformable wall 15 may present deformation that is permanent or temporary when the appliance 13 returns to its retracted position inside the tube 5. Furthermore, the deformation may be the result not of applying a mechanical force as explained above, but rather of applying optionally ionizing heat, for example.

According to an advantageous characteristic, the distal portion 7 of the insertion tube 5 includes a guide system 19 for guiding the appliance 13 so as to ensure that the deformable wall 15 expands radially during the movement of the appliance. As can be seen more clearly in FIGS. 2 and 4, the guide system 19 is in the form of a ramp or a cone opening out into the bore 12 and serving to guide the appliance 13 progressively so that it passes from its retracted position to its working position.

From the above description, it can be seen that when the appliance 13 is in its retracted position, the outlet section 8 of the distal portion 7 of the instrument 1 corresponds to the right cross-section of the insertion tube 5 (FIGS. 1, 2). In other words, when the appliance 13 is in the retracted position, the distal portion 7 of the instrument 1 presents a right cross-section that is equal to the right cross-section of the insertion tube 5, said distal portion 7 of the instrument 1 not including any extra thickness outside the insertion tube 5. Thus, with the appliance 13 in the retracted position, the insertion tube 5 presents a right cross-section that is constant over the entire length from its proximal portion 6 to its distal portion 7.

When the distal portion 7 occupies a position in which the appliance 13 is to be taken in its outlet section 8, the sliding or movement of the appliance 13 relative to the tube 5 leads to radial deformation of the deformable wall 15 so that at its outlet section 8 the section of the outlet orifice 11 increases (FIGS. 3, 4). In other words, in the working position, the outlet section 8 of the distal portion 7 of the insertion tube 5 is greater than the outlet section 8 of the distal portion 7 of the insertion tube 5 when the appliance 13 is in its retracted position. The insertion tube 5 thus possesses an outlet section 8 that increases when the appliance 13 goes from a retracted position to a working position. It should be observed that the right cross-section of the insertion tube 5 is increased over an axial length that is limited to no more than the distal portion 7 of the insertion tube 5. Typically, the distal portion 7 of the insertion tube 5 that presents a variation in its right cross-section as a result of the appliance corresponds to an axial length that is less than or equal to twice the diameter of the insertion tube 5.

The increase in the diameter of the distal portion 7 allows various appliances 13 to be delivered while avoiding damage to surrounding tissue. It is thus possible to have available at the distal portion of the instrument 1 an appliance 13 that presents a size or an outlet section that is considerably greater than the outlet section of the orifice 11 at rest.

Figure 5:
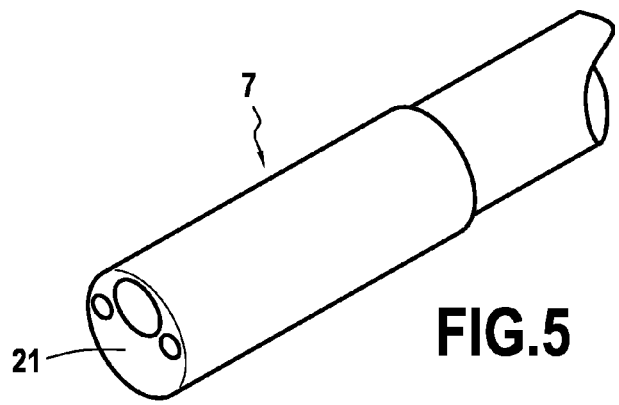
FIGS. 5 to 7 are fragmentary views in perspective of the distal portion of the instrument in accordance with the invention in various characteristic utilization positions.
Figure 6:
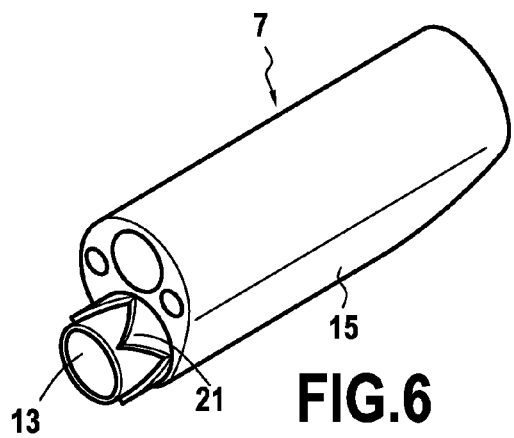

According to an advantageous characteristic of the embodiment of the invention shown more particularly in FIGS. 5 and 6, the distal portion 7 of the insertion tube 5 is provided with a sealing member 21 that closes the outlet orifice 11 of the passage for the appliance. This sealing member 21 is an ejectable plug, a tearable membrane, etc., with ejection or tearing etc. being performed by the appliance 13 or by fluid pressure. The sealing member 21 thus closes the outlet orifice 11. As can be seen more precisely in FIG. 6, the sliding of the appliance 13 for extending it from the end of the distal portion 7 leads to the sealing membrane 21 being deformed or torn (or to the sealing plug being ejected). Naturally, the delivery of a fluid under pressure to the outlet orifice 11 may also serve to eliminate the sealing member 21.

Figure 7:
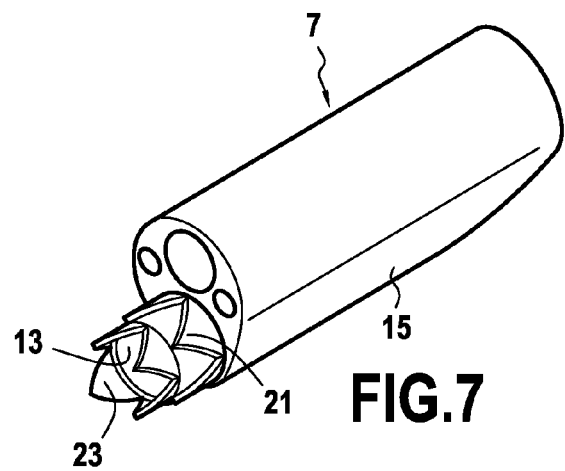

According to another advantageous embodiment characteristic shown in FIG. 7, the distal portion 7 of the tubular duct is provided with at least one sealing envelope 23. This sealing envelope 23 is tearable by the tooling housed inside the tubular duct. Advantageously, this sealing envelope 23 presents greater resistance than the sealing member 21 carried by the distal portion 7.

The invention is not limited to the examples described and shown since various modifications may be applied thereto without going beyond its ambit.

The invention claimed is:

1. An endoscope instrument comprising an insertion tube possessing a proximal portion for connection to an actuation support and a distal portion presenting an outlet section occupied, firstly, by a viewing zone and, secondly, by at least one outlet orifice of a passage for at least one appliance mounted inside the insertion tube by the proximal portion for occupying a retracted position inside the tube and a working position in which the appliance occupies at least a portion of the outlet section, the cross-section of the appliance being greater than the cross-section of the outlet orifice in the retracted position of the appliance, the instrument being characterized in that the distal portion of the insertion tube includes at least one radially deformable wall over only a portion of its length extending from the outlet section, and in that the insertion tube includes, in its distal portion, a guide system opening out into the passage for guiding the appliance in order to enable the deformable wall to be expanded radially during the movement of the appliance thereby enabling the surface of the outlet section of the distal portion of the tube to be increased on the appliance passing from its retracted position in which the appliance does not stress the deformable wall to its working position in which the deformable wall is stressed radially, the outlet section of the distal portion corresponding to the right cross-section of the insertion tube in the retracted position of the appliance.

2. A medical instrument according to claim 1, characterized in that the distal portion of the insertion tube is provided with a sealing member closing the outlet orifice of the passage for the appliance.

3. An instrument according to claim 2, characterized in that the sealing member is a plug that is ejectable or a membrane that is tearable by the appliance or by fluid pressure.

4. An instrument according to claim 1, characterized in that the appliance includes at least one tool mounted in the tubular duct.

5. An instrument according to claim 1, characterized in that the distal portion of the tubular duct is provided with at least one sealing envelope.

6. An instrument according to claim 5, characterized in that the sealing envelope presents mechanical strength that is greater than that of the sealing member carried by the distal portion of the insertion tube.

7. An instrument according to claim 5, characterized in that the sealing envelope of the tubular duct is an envelope that is tearable by the tooling housed inside the tubular duct.

8. An instrument according to claim 1, characterized in that the distal portion of the insertion tube defines the passage for the appliance.

9. An instrument according to claim 1, characterized in that the distal portion of the insertion tube includes a viewing system.

10. An instrument according to claim 9, characterized in that the viewing system is embedded in the deformable wall.

11. An instrument according to claim 1, characterized in that the distal portion is removable relative to the insertion tube.

12. An endoscope, characterized in that it includes at least one instrument in accordance with claim 1.

* * * * *